(12) United States Patent
Traneus et al.

(10) Patent No.: US 11,798,674 B2
(45) Date of Patent: Oct. 24, 2023

(54) STATIC DEVICE FOR USE IN RADIOTHERAPY TREATMENT AND DESIGN METHOD FOR SUCH A DEVICE

(71) Applicant: RaySearch Laboratories AB, Stockholm (SE)

(72) Inventors: Erik Traneus, Uppsala (SE); Björn Hårdemark, Enskededalen (SE)

(73) Assignee: Raysearch Laboratories AB, Stockholm (SE)

( * ) Notice: Subject to any disclaimer, the term of this patent is extended or adjusted under 35 U.S.C. 154(b) by 0 days.

(21) Appl. No.: 17/660,425

(22) Filed: Apr. 25, 2022

(65) Prior Publication Data

US 2022/0344027 A1 Oct. 27, 2022

(30) Foreign Application Priority Data

Apr. 26, 2021 (EP) .................................... 21170560

(51) Int. Cl.
*G16H 20/40* (2018.01)
*A61N 5/10* (2006.01)

(52) U.S. Cl.
CPC ............ *G16H 20/40* (2018.01); *A61N 5/103* (2013.01); *A61N 5/1031* (2013.01); *A61N 5/1043* (2013.01); *A61N 2005/1087* (2013.01); *A61N 2005/1095* (2013.01); *A61N 2005/1096* (2013.01)

(58) Field of Classification Search
CPC .............. A61N 5/10; A61N 2005/1087; A61N 2005/1095
See application file for complete search history.

(56) References Cited

U.S. PATENT DOCUMENTS

2013/0230145 A1* 9/2013 Slatkin ................. A61N 5/1077
378/65

FOREIGN PATENT DOCUMENTS

EP       3957361 A1    2/2022
WO    2020099510 A2    5/2020

OTHER PUBLICATIONS

Sakae et al., 'Multi-layer energy filter for realizing conformal irradiation in charged particle therapy', Feb. 2000, Med. Phys. 27 (2) (Year: 2000).*

(Continued)

*Primary Examiner* — Eliza W Osenbaugh-Stewart
(74) *Attorney, Agent, or Firm* — Noréns Patentbyrå AB (57) ABSTRACT

A compensating device for use in ion-based radiotherapy may comprise a disk with a number of protrusions may be placed in a radiation beam to affect the ions in the beam in different ways to create an irradiation field from a broad beam. This is particularly useful in FLASH therapy because of the limited time available or modulating the beam. A method of designing such a compensating device is proposed, comprising the steps of obtaining characteristics of an actual treatment plan comprising at least one beam, determining at least one parameter characteristic of the desired energy modulation of the actual plan by performing a dose calculation of the initial plan and, based on the at least one parameter, computing a shape for each of the plurality of elongated elements to modulate the dose of the delivery beam to mimic the dose of the initial plan per beam.

10 Claims, 3 Drawing Sheets

(56) References Cited

OTHER PUBLICATIONS

Yuri Simeonov et al: "3D range-modulator for scanned particle therapy: development, Monte Carlo simulations and experimental evaluation", Physics in Medicine and Biology, Institute of Physics Publishing, Bristol, GB, vol. 62, No. 17, Aug. 11, 2017, pp. 7075-7096.
Extended European Search Report, dated Oct. 26, 2021, European Patent Office, Munich, Germany.

* cited by examiner

STATIC DEVICE FOR USE IN RADIOTHERAPY TREATMENT AND DESIGN METHOD FOR SUCH A DEVICE

TECHNICAL FIELD

The present invention relates to a passive device for use in radiotherapy treatment and to a method of designing such a device.

BACKGROUND

In ion-based radiotherapy treatment, a patient is irradiated with a beam of protons or some other type of ion. Ion-based treatment is advantageous because the volume in which each ion deposits its energy can be controlled with high precision by controlling the ion's energy and direction. A common way of achieving a homogeneous or in-homogeneous irradiation field is to use pencil beam scanning in which many small beams of different directions and energy levels are directed at different points within the target. The term pencil beam scanning includes a number of different scanning methods, such as spot scanning, or line scanning or raster scanning.

In some cases, however, it is desirable to shape and modulate the field using a static broad beam with a single energy in combination with different types of active or passive devices to shape the field.

It is known in ion-based radiotherapy to use passive devices such as compensators to control the maximum range of the ions by providing an element of varying thickness made from a material that will attenuate the energy of the ions, thus shortening their path in dependence of the thickness of the compensator.

The point in which an ion deposits the main part of its energy is known as the Bragg peak, and is well defined near the end of the ion's trajectory. In addition to affecting the position of the Bragg peaks by means of compensators, devices for spreading the Bragg peaks in the depth direction to achieve homogeneous dose coverage over the target volume are known. To achieve this, a rotating disk having areas of different thicknesses is commonly used and rotating at approximately 30 rounds per second has been used. Other devices include ripple filters, also called ridge filters, which are devices comprising a disk with a regular pattern of ridges that will modulate the beams to broaden Bragg peaks in the depth direction.

In recent years, FLASH therapy has become of interest, as it promises efficient treatment in shorter and fewer fractions, with additional benefits therefore saving hospital resources and also more efficient from the point of view of the patient. In FLASH therapy, treatment irradiation is given in very short pulses of very high dose rates, typically a fraction of a second at a dose rate of 40 Gy/s or more. The time aspect is critical for achieving the advantages associated with FLASH treatment. With such short times, treatments with scanning beams must be given at one single energy level, since every change in the energy level takes on the order of magnitude of one second. Traditional pencil beam scanning methods therefore do not work. Further, the rotating disk used in conventional passive therapy to create the spread-out Bragg peak also will not be feasible.

Simeonov et al.: 3D range-modulator for scanned particle therapy: development, Monte Carlo simulations and experimental evaluation; 2017 Phys. Med. Biol. 62 7075, propose a static element comprising a disk of varying thickness effectively functioning as a compensator and with a number of thin pins with a well-defined shape and different lengths arranged on a surface of the disk to modulate the necessary shift of the Bragg peak. This element combines the function of a compensator and energy filter in such a way as to allow PBS plans to be delivered with only a single energy layer per beam to reduce delivery time. The element is designed by means of ray tracing combined with the concept of radiological path length, based on the patient's geometry and the desired dose in the target. In practice this involves following a number of lines of sight through the patient, registering the depths where the line intersects with the proximal and distal surface of the target. The disk part is designed with varying thickness to serve as a compensator adapted to the distal surface of the target and the proximal-distal distance is used to calculate the lengths and shape of the pins in such a way that the field will cover the whole target. This method enables a static device that is able to create a homogeneous or near homogeneous dose distribution conformed to both the distal and the proximal edge of the target. The device may be manufactured by 3D printing.

There is a desire to be able to create a more complex dose distribution, for example, to enable co-optimization of overlapping fields.

Co-pending patent application EP20192106.1 discloses a method of designing a compensating device for use in ion-based radiotherapy treatment delivery, the device including a substantially disk-shaped structure including on one side of the disk a plurality of elongate elements. The design method involves adapting the shape of each one of the elongate elements based on characteristics of an actual treatment plan, by determining at least one parameter characteristic of the desired energy modulation of the actual plan by performing a dose calculation of the initial plan and, based on the at least one parameter, computing a shape for each of the plurality of elongate elements to modulate the dose of the delivery beam to mimic the dose of the initial plan per beam.

SUMMARY OF THE INVENTION

It is an object of the present invention to provide a design method for a compensating device as discussed above.

The disclosure relates to a method of designing a compensating device for use in ion-based radiotherapy treatment delivery, said device including a substantially disk-shaped structure including on one side of the disk a plurality of elongate elements, said method comprising the steps of obtaining a model of the compensating device with its properties defined by a set of model parameters, obtaining an optimization problem, said optimization problem defining planning objectives, optimizing the values of a set of planning parameters to achieve the planning objectives, the planning parameters including the parameters in the set of model parameters.

Typically, the planning parameters also include standard planning parameters such as spot weights. The planning objectives are typically defined to ensure uniform dose to a target while sparing other tissues and in particular organs at risk. The step of obtaining an optimization problem may include formulating an optimization problem based on the current patient anatomy, or using a pre-formulated optimization problem.

Obtaining a suitable optimization problem and using it to optimize the compensating device enables a fast and reliable design of a compensating device as defined. It also enables other advantageous aspects to be considered in the design process, for example robustness, linear energy transfer (LET) based objectives or relative biological effect (RBE) based objectives.

The method may also include selecting a material for the elongate body or bodies. Alternatively, the material may have been selected beforehand. The combination of shape and material properties determines how the beam is affected by the elongate element. The elongate bodies are typically defined by the shape and dimensions of their base, and their height.

The plan resulting from the optimization procedure may be used as a final plan for delivery to the patient, either as it is or after additional optimization steps after the compensating device has been designed. In the latter case, the method comprises the step of re-optimizing the standard planning parameters and taking the parameters of the compensating device into account. This is preferably done without involving the planning parameters of the compensating device in the optimization.

To prepare for production of the resulting compensating device, the method may comprise the step of obtaining element shape data indicating the shape of each elongate element, based on the planning parameters of the compensating device, and using the element shape data to generate a file comprising instructions for the design of the compensating device. The file may be used to control a manufacturing process, performed, for example by a 3D printer.

The treatment plan may be a pencil beam scanning plan or a broad beam plan such as a double scattering plan or a single scattering plan with a single energy, that is, without a spread-out Bragg peak. As mentioned above, the term pencil beam scanning covers a number of different scanning methods, including spot scanning, line scanning or raster scanning.

The disclosure also relates to a method of manufacturing a compensating device for use in ion-based radiotherapy treatment delivery, comprising performing the method according to any one of the preceding claims, and using the shape data resulting from the plan to generate a file comprising instructions for the design of the compensating device, and using the file to control the manufacturing.

The disclosure also relates to a computer program product comprising computer-readable code means which, when run in a computer will cause the computer to perform the method according to any one of the embodiments discussed above. The computer product may comprise a non-transitory storage holding the code means.

The disclosure also relates to a computer system comprising a program memory and a processing means arranged to execute a program found in the program memory, said program memory comprising a computer program product according to the above.

The compensation device is suitable for use with different types of ion-based radiotherapy treatment. It is well suited for use in FLASH therapy since it is a passive component that works without any moving parts during the treatment; however, it may be used also for conventional therapy. It will enable a reduction in the number of energy levels used during treatment, and even enable full target coverage using only one energy level.

The design method herein described allows complex criteria to be considered when designing the compensator element, since any desired criterion may be expressed as part of an initial optimization problem, including variable RBE dose optimization, LET objectives and beam specific objective functions. Therefore, co-optimization of overlapping fields is enabled. Robust optimization with respect to uncertainties in factors such as patient position and density may also be applied, which will result in a plan that will work more reliably in different scenarios.

The method may further comprise designing a channel array device to be used together with a compensator device, said channel array device including a substantially disk-shaped structure including an array of channels.

In some embodiments, the channel array device may be designed after the compensating device, taking into account the design of the compensating device. In this case, the method may further comprise
obtaining a model of the channel array device with its properties defined by a set of model parameters,
obtaining an optimization problem, said optimization problem defining planning objectives for the channel array device in view of the planning parameters obtained for the compensation device,
optimizing the values of a set of planning parameters to achieve the planning objectives, the planning parameters including the parameters in the set of model parameters for the channel array device.

In other embodiments, the compensating device and the channel array device are optimized together in one process. In this case, the method includes the following steps: obtaining an optimization problem, defining joint planning objectives for the compensating device and the channel array device to function together, and optimizing the values of a set of joint planning parameters for the compensating device and the channel array device to achieve the joint planning objectives.

In all embodiments, a start guess of channel array parameters can be obtained by using the ray-trace method and a simple geometrical consideration where the channel area is proportional to the desired fluence at the location of the channel. The channel array device may be manufactured in the same way as the compensating device, either together with the compensating device or in a separate operation.

The purpose of the channel array device is to reduce the amount of modulation in the incident proton fluence required to meet the planning goals. The depth and size of a channel determine how many of the incident protons that pass through the array device disk in a region near each channel. This will affect the dose in the regions downstream of the channel. In an ideal situation it will thereby be possible to have a homogenous incident fluence and still achieve dose distributions where a laterally modulated fluence would be required without the channel array device. This allows the compensating device of the first disclosure to be use for broad beam irradiation. The shape and arrangement of the channels can be determined through either a ray-tracing method or, through an optimization method.

The ray-tracing method applies as a starting point the fluence of an existing plan. The particle fluence distribution of the existing plan is then used to compute the size and distribution of the channel voids needed to reproduce the fluence of the existing plan for a given incident fluence.

Typically, the planning parameters also include standard planning parameters such as spot weights. The planning objectives are typically defined to ensure uniform dose to a target while sparing other tissues and in particular organs at risk. An additional planning objective can be that the solution should yield an incident fluence that is as uniform as possible or have any other desired shape. The step of obtaining an optimization problem may include formulating an optimization problem based on the current patient's anatomy, or using a pre-formulated optimization problem.

The use of the channel array device in combination with the compensating device allows 3D conformal dose to be delivered also for broad beam irradiation.

The disclosure also relates to a computer program product comprising computer-readable code means which, when run in a computer will cause the computer to perform the method according to any one of the embodiments discussed above. The computer product may comprise a non-transitory storage holding the code means.

The disclosure also relates to a computer system comprising a program memory and a processing means arranged to execute a program found in the program memory, said program memory comprising a computer program product according to the above.

BRIEF DESCRIPTION OF DRAWINGS

The invention will be described in more detail in the following, by way of examples and with reference to the appended drawings.

DETAILED DESCRIPTION OF EMBODIMENTS

Figure 1:
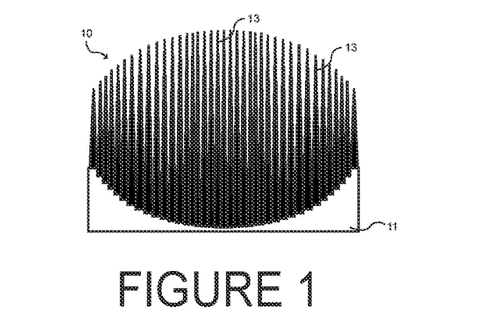
FIG. 1 illustrates an example of a device as disclosed in this description.

FIG. 1 shows an example of a passive modulation device 10 according to embodiments of the invention. The device comprises a compensator element 11 which is essentially a disk having varying thickness across its area. The thickness is designed to cause an incoming radiation field to conform to the distal end of the target. On the disk a number of protrusions in the form of spike-shaped structures 13 are arranged, typically of the same material as the compensator element. The protrusions 13 are typically placed in a grid pattern on the disk, each occupying an area of, for example, 1.5×1.5 mm$^2$ of the disk. The protrusions 13 have different heights and shapes, selected in such a way that a beam passing through the device will be modulated to have Bragg peaks covering the whole of a target in a desired way. Of course, the size, shape and thickness of the compensator element, the arrangement of the protrusions on the compensator element and their size and heights, should be selected to conform to the target including suitable margins.

Figure 2A:
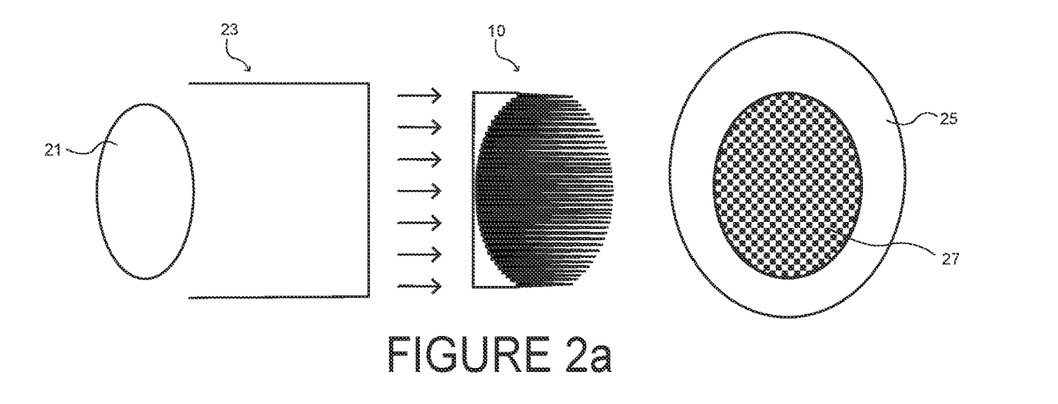
FIG. 2a illustrates how the device of FIG. 1 may be applied in radiation therapy.

FIG. 2a shows the device of FIG. 1 inserted between a source 21 of radiation emitting a homogeneous radiation field 23, and a patient 25, shown simplified as an elliptic form and comprising a target 27. The radiation field is modulated by the device 10 in such a way that the energy spectrum of the radiation after passing through the device will create a dose field that conforms to the shape of the target. In FIG. 2a, the target is shown to have a simple nearly circular form but according to the invention, more complex shapes can be treated as well.

Figure 2B:
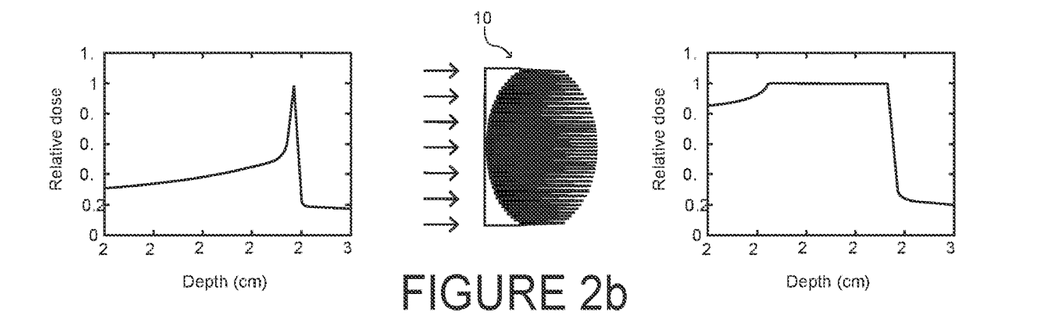
FIG. 2b illustrates the dose depth of the incoming beam upstream of the device and the resulting depth dose distribution in the patient.

FIG. 2b corresponds to the situation of FIG. 2a. The diagram on the left depicts the depth dose of the incoming beam upstream of the device. As can be seen, most of the dose would be deposited at one particular depth, corresponding to the energy of the protons in the beam. The diagram on the right depicts the depth dose after the beam passes through the modulation device 10. As can be seen, the depth dose has a broader range, corresponding to dose deposition throughout the target 27. Although FIGS. 2a and 2b show the modulation device 10 inserted in the beam with the protrusions 13 downstream of the disk 11, it could also be placed in the opposite direction, that is with the protrusions upstream of the disk.

According to the invention, the modulation device is optimized by direct optimization of its geometry parameters. These parameters typically include the thickness of the compensator 11 and the width and length of each of the protrusions. The width and cross section shape may vary over the length of each protrusion. A pixel grid pattern may be included as a constraint in the optimization problem, or may be an optimization parameter in the optimization problem. The pixel grid pattern defines the base of each of the protrusions where they connect with the compensator 11. Alternatively, the base of each protrusion may be selected freely in the optimization.

The protrusion designed for each pixel does not have to be shaped as a pin or have any type of symmetry, although a circular symmetry may be easier to achieve than a more complex shape. It can instead be any type of elongate body, or set of elongate bodies, extending from the compensator element in a direction parallel with the beam. It could be composed of a number of different protrusions, such as spikes, pins or elongate sheets, within one pixel. The lengths of different fractions of the elongate body or bodies extending in one pixel are such that the ions passing through that pixel will be affected differently to result in a spectrum of absorbed energy.

Figure 3A:
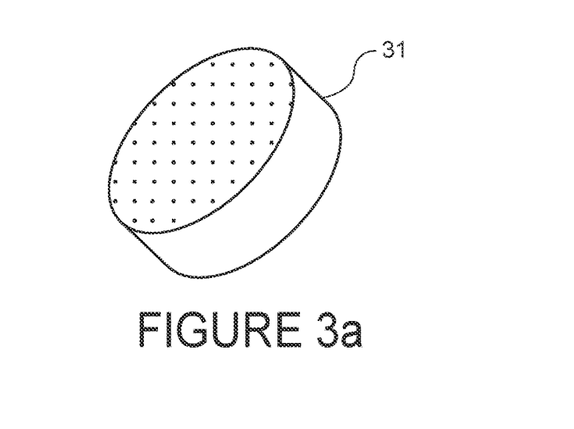
FIG. 3a illustrates a channel array device that may be used together with the device shown in FIG. 1.

FIG. 3a shows a channel array device with an array of open pipes or channels which may be used together with the modulation device described in FIGS. 1, 2a and 2b, or with any other compensating device used in ion therapy. The channel array device preferably made from a high Z material and is shaped as a disc having an array of narrow channels, or channels extending through the disc to a depth that is specific per channel. Each channel may have any suitable cross-section, for example circular or square. The size is tuned to block a certain amount of proton fluence. The removal of protons will result in non-uniform dose at shallow depths. Due to scattering effects and initial emittance of the beam the dose from neighboring channels will merge further downstream from the channel array device as depth increases to yield sufficiently smooth dose in the target. The dose non-uniformity at shallow depths is in fact beneficial as it actually enhances the sought FLASH effect in upstream risk organ tissues. The channel array device may be designed in any suitable way but preferably by optimization as will be discussed in more detail below.

Figure 3B:
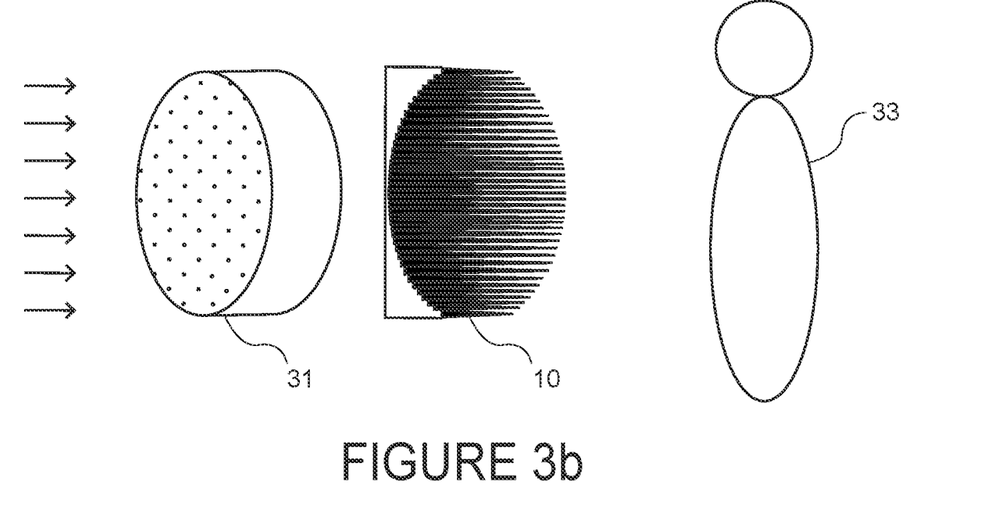
FIG. 3b illustrates an assembly of the channel array device of FIG. 3a and a compensator device such as the device shown in FIG. 1.

FIG. 3b shows an arrangement of the channel array device of FIG. 3a used together with a compensating device, which may be a modulating device 10 as discussed above. In FIG. 3b the channel array device is placed upstream of the compensating device, but it may also be placed downstream.

When used together with a modulating device 10, the channels of the channel array device may be, but are not necessarily, placed in the same grid pattern as the protrusions of the modulating device, so that each channel will be aligned with the longest portion of one of the protrusions, in the direction of the beam. When used together with a compensating device that does not include an array or a grid pattern, the channels may be placed in any suitable way.

The modulating device and the channel array device may be two separate units that are used together as discussed above, but they may also be joined together, or manufactured as an integrated unit.

Figure 4:
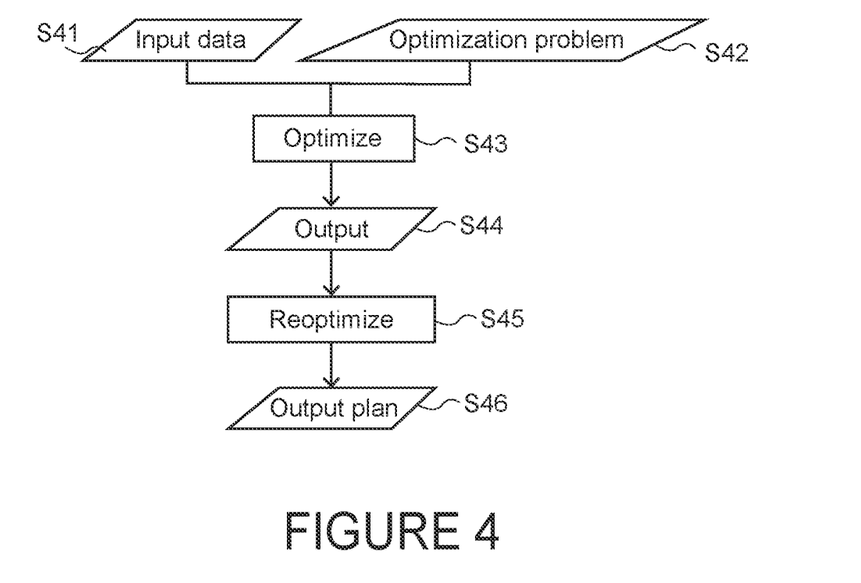
FIG. 4 is a flow chart of one method for designing the modulation device.

FIG. 4 is a flow chart of a method that may be used for designing the modulating device 10. Input data S41 to this method includes a set of planning parameters for the modulating device, including in some embodiments the thickness of the disk 11, the shape and size of the base of each of the protrusions 13 and the length of each protrusion. Alternatively, the shape and/or size of the base of the protrusions may be predefined and added as a constraint. As mentioned above, the protrusions can have any suitable shape, and may even have different shapes and/or sizes with respect to their bases as well as their lengths.

Initially, an optimization problem S42 to be used for optimizing the modulating device is also obtained. The optimization problem comprises objective functions and/or constraints related to the how the incoming radiation should be affected by the modulating device. In step S43, the optimization is performed, based on the optimization problem.

As an example, the optimization problem for the modulation device can be setup as described by the steps below:

Define a cartesian grid (same pitch in horizontal and vertical direction) defining lateral positions of the elongated bodies.

At grid point (pixels) that are inside the field place an elongated body.

Give the elongated bodies the shape of a pyramid with quadratic base and truncated at a certain height.

The side of the pyramid base is the same or smaller than the pitch of the cartesian grid.

The geometry of each pyramid is specified by the size of the base, the height and the size of the quadratic surface and the tip of the truncated pyramid.

Each pyramid is placed on a solid volume representing the compensator. The compensator has same base size as the grid pitch and a heigh whose value is subject for optimization.

During the optimization process the geometry parameters of the pyramids are varied until an optimal geometry is found.

The geometry parameters are optimized together with other parameters such as spot weights of optimized separately.

The specification above is given as an example. The channel array device can be part of the overall optimization or be optimized separately. Suitable parameters for optimization are the diameters of the holes.

The resulting shape data S44 for each elongate body or set of bodies may be used for triangulation to generate a CAD file that may be used for producing the compensating device, for example, by 3D printing. Alternatively, some additional optimization steps S45 may be performed, to improve the resulting compensating device before it is produced, i.a. by taking into account possible scattering from the elongate bodies before the final shape data is output in S46.

One or more further additional optimization steps may be included, after determining the geometry of the compensating device per beam, performing a final PBS re-optimization taking the fixed geometry of the compensating device into account in the re-optimization. This will help fine tune the plan further. The final optimization is performed with a single energy layer per plan. The final optimization can include multiple beams and any type of advanced objective function such as functions related to RBE dose, LET or robustness.

Alternatively, the additional optimization can be done with multiple energy layers. If the design and effect of the compensation device are perfect, the optimized plan should place all weights in a single energy layer. If the layer weight spread is above some limit this data can be used to adjust the geometry of the compensating device. This procedure can be iterated until the compensation device geometry is stable between iterations. A similar approach should be possible to apply to optimization of standard compensators for passive planning.

As mentioned above, the resulting modulating device may be used to shape and modulate the field for any type of ion-based radiation treatment. In particular, it will enable a reduction in the number of energy layers used, making the delivery of the treatment faster. Preferably, delivery using only one energy layer is enabled by designing the elongate bodies so that they ensure coverage of the whole, three-dimensional target from one field.

Figure 5:
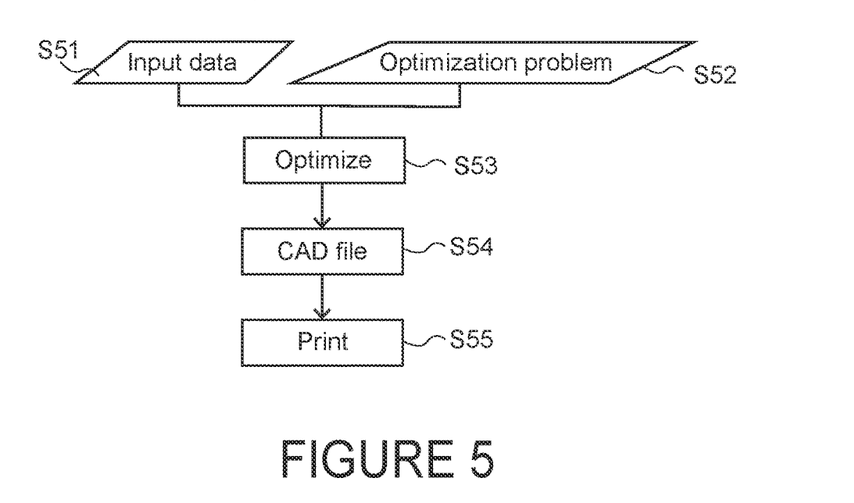
FIG. 5 is a flow chart of one method for designing the channel array device.

FIG. 5 is a flow chart of a method that may be used for designing the channel array device 31. In this embodiment, the channel array device 31 is designed to be used together with an existing modulating device or compensating device. Input data S51 to this method is the geometry of a compensating device or modulating device 10 to be used together with the channel array device, and a proton fluence distribution of a scanned beam or a broad beam. Input data also include a set of model parameters for the channel array device, such as thickness and number and dimension of channels. An optimization problem is also obtained, defining planning objectives for the channel array device 31 in view of the planning parameters obtained for the compensation device 10. The compensating or modulating device may be a modulating device 10 as discussed in connection with FIG. 1. The compensating or modulating device may have been designed by the method discussed in connection with FIG. 4, by the methods discussed in the above mentioned co-pending application, or by any other method. The treatment plan may be a FLASH plan, involving a broad beam proton fluence distribution or a FLASH plan using pencil scanning delivery.

In step S53, the channel array device 31 is optimized based on the input data S51 and the optimization problem S52, having properties that are defined by a set of model parameters including for example the thickness of the channel array device and the channel dimensions. The geometry of the compensating device is used to determine the number of channels, and their positions. The number of channels, and their positions, can also be determined independent from the geometry of the compensating device. The thickness of the channel array plate should be sufficient to completely stop an incident particle that does not pass through a channel void.

The channels may be of cylindrical shape with the cylinder axis along the beam direction or any other suitable shape. For cylindrical shaped channels the diameter is determined either by a geometrical ray-trace method where the transmission is proportional to the channel's cross section area. The channel diameters can also be determined through a direct optimization method where the diameters are free variables subject for optimization together with other free variables of the optimization problem such as spot weights and geometry parameters of the compensating device.

As a final step S54, the shape information per channel is then used to generate control data that may be used to manufacture the device. This may involve using the shape information for triangulation to generate a CAD file which may be used for manufacturing the device. For example the CAD file may be sent to a 3d-printer which, an optional step S55 will print the device according to the information in the CAD file. Of course, another suitable manufacturing method may be used.

Figure 6:
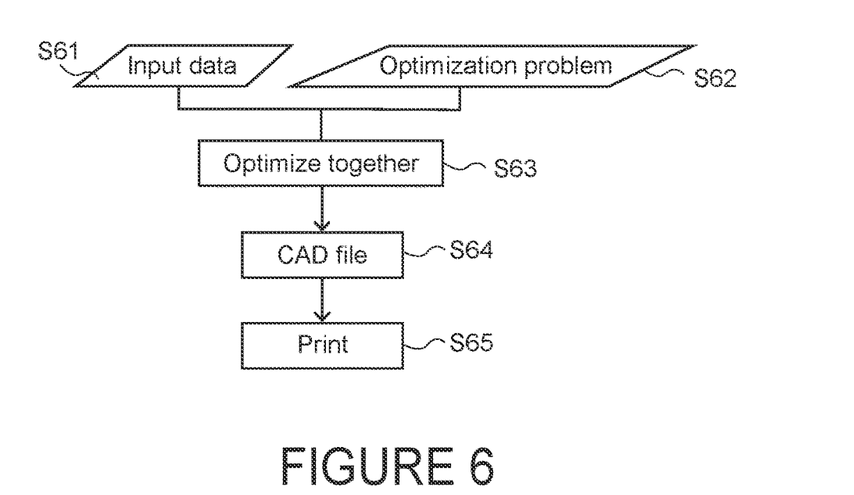
FIG. 6 is a flow chart of a method for designing the modulation device and the channel array device together.

FIG. 6 is a flow chart of an alternative method in which the channel array device 31 is designed together with the compensator device or modulator device 10. The channel array device has the same properties as discussed in connection with FIG. 5. In this embodiment, input data S61 include a set of joint planning parameters for the combination of compensator device and channel array device is obtained, including the shape and size of the compensator or modulator device and the channel array device and the distance between them during treatment. An optimization problem S62 defines joint planning objectives for the combination of the modulating device 10 and the channel array device 31 in view of the joint planning parameters. In step S63, the modulator device 10 and the channel array device 31 are optimized together to fulfil the joint planning objectives. In step S64, control data are generated based on the parameters determined in the optimization in the same way as in step S54. As before, step S65 is an optional step of manufacturing the modulating device 10 or other compensator device and the channel array device 31.

In all embodiments, the modulating device 10 and the channel array device 31 may be positioned at a distance from each other or adjacent each other, substantially concentrically with respect to the direction of the beam.

Figure 7:
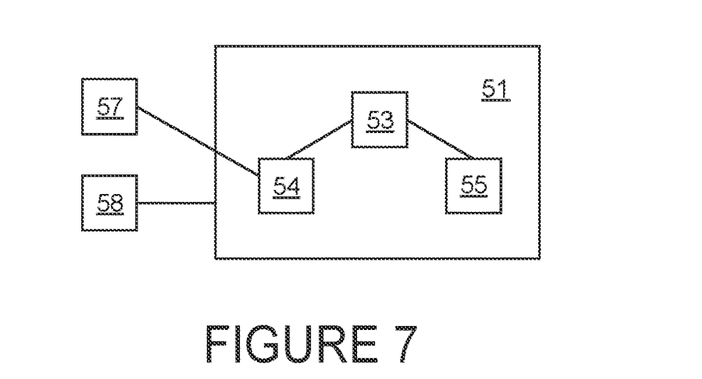
FIG. 7 is a schematic drawing of a computer system in which the inventive method may be carried out.

FIG. 7 is a schematic overview of a computer system in which the optimization according to the invention may be carried out. A computer 51 comprises a processor 53, a data memory 54 and a program memory 55. Preferably, one or more user input means 57, 58 is also present, in the form of a keyboard, a mouse, a joystick, voice recognition means and/or any other available user input means. The user input means may also be arranged to receive data from an external memory unit.

The invention claimed is:

1. A computer-based method of designing a compensating device for use in ion-based radiotherapy treatment delivery, the device including a substantially disk-shaped structure including on one side of the disk a plurality of elongate elements, the method comprising:
obtaining a model of the compensating device with its properties defined by a set of model parameters, wherein the model parameters include a pixel grid pattern, a thickness of the disk-shaped structure, and widths and lengths of the respective elongate elements,
formulating an optimization problem based on data pertaining to a patient's anatomy, the optimization problem defining planning objectives with respect to dose delivery to a target while sparing other tissues and organs at risk of the patient,
optimizing the values of a set of planning parameters for the compensating device to achieve the planning objectives, the planning parameters including the set of model parameters, wherein the optimization is performed with respect to one or more of variable RBE dose optimization, LET objectives, or beam specific objective functions,
generating a computer-readable file including manufacturing instructions for use by manufacturing equipment for the compensating device, the manufacturing instructions including shape data for manufacturing the plurality of elongate elements of the compensating device, wherein the shape data is determined at least in part based on the optimized values for the set of planning parameters for the compensating device, and
transmitting the computer-readable file to a recipient, to be used by manufacturing equipment when manufacturing the compensating device.

2. The method of claim 1, wherein the optimizing step also includes selecting a material for the elongate elements.

3. The method of claim 1, further comprising:
generating a treatment plan to be used in treatment delivery to a patient, wherein the treatment plan is a pencil beam scanning plan or a double scattering plan or a single scattering plan and takes into account the optimized values of the set of planning parameters for the compensating device.

4. The method of claim 1 further comprising designing a channel array device to be used together with the compensating device, the channel array device comprising a substantially disk-shaped element having an array of channels, the method further comprising, for designing the channel array device, obtaining a model of the channel array device with its properties defined by a set of model parameters, obtaining an optimization problem for the channel array device, the optimization problem defining planning objectives for the channel array device in view of the planning parameters obtained for the compensation device, optimizing the values of a set of planning parameters for the channel array device to achieve the planning objectives for the channel array device, the planning parameters including the parameters in the set of model parameters for the channel array device.

5. The method of claim 1, further comprising designing a channel array device to be used together with the compensating device, the channel array device comprising a substantially disk-shaped element having an array of channels, the method further comprising, for designing the channel array device, obtaining an optimization problem defining joint planning objectives for the compensating device and the channel array device to function together, and optimizing the values of a set of joint planning parameters for the compensating device and the channel array device to achieve the joint planning objectives.

6. A method of manufacturing a compensating device for use in ion-based radiotherapy treatment delivery, comprising:
receiving a computer-readable file generated according to claim 1, and
using the manufacturing instructions in the received computer-readable file to control 3D-printing equipment used to manufacture the compensating device.

7. A computer program product comprising computer-readable code means which, when run in a computer will cause the computer to perform the method according to claim 1.

8. The computer program product of claim 7 comprising a non-transitory storage holding the code means.

9. A computer system comprising a program memory and a processor arranged to execute a program found in the program memory, the program memory comprising a computer program product according to claim 8.

10. The method of claim 1, further comprising:
    re-optimizing planning parameters that are not planning parameters of the compensating device, wherein the re-optimizing takes into account the optimized planning parameters of the compensating device.

* * * * *